(12) United States Patent
Denmark

(10) Patent No.: US 8,789,243 B2
(45) Date of Patent: Jul. 29, 2014

(54) DISPOSABLE HANDLE COVER FOR A SURGICAL LIGHTHEAD

(71) Applicant: Ecolab USA Inc., St. Paul, MN (US)

(72) Inventor: Wayne Douglas Denmark, Columbus, MS (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 13/622,730

(22) Filed: Sep. 19, 2012

(65) Prior Publication Data

US 2014/0075721 A1 Mar. 20, 2014

(51) Int. Cl.
*B25G 1/10* (2006.01)
*A61B 19/00* (2006.01)
*F21V 21/40* (2006.01)

(52) U.S. Cl.
USPC .............. 16/421; 16/906; 362/804; 362/399

(58) Field of Classification Search
CPC ............ B25G 1/102; B25G 3/32; B25G 1/04; E05B 1/0015; F21V 21/403
USPC ......... 16/421, 422, 436, 110.1, 906; 362/399, 362/804
See application file for complete search history.

(56) References Cited

U.S. PATENT DOCUMENTS

| 4,559,671 | A | * | 12/1985 | Andrews et al. ................. 16/421 |
| 4,605,124 | A | * | 8/1986 | Sandel et al. ................... 206/223 |
| 4,844,252 | A | * | 7/1989 | Barron et al. .................. 206/223 |
| 4,878,156 | A | * | 10/1989 | Hallings et al. ............... 362/109 |
| 4,974,288 | A | * | 12/1990 | Reasner .......................... 16/421 |
| 4,975,826 | A | * | 12/1990 | Bell ............................. 362/376 |
| 4,976,299 | A | * | 12/1990 | Bickelman ..................... 150/155 |
| 5,036,446 | A | * | 7/1991 | Quintanilla et al. ........... 362/399 |
| 5,065,296 | A | * | 11/1991 | Cude ............................. 362/399 |
| 5,156,456 | A | * | 10/1992 | Hoftman et al. .............. 362/400 |
| 5,188,454 | A | * | 2/1993 | Quintanilla et al. ........... 362/399 |
| 5,273,157 | A | * | 12/1993 | Spina ............................ 206/223 |
| 5,355,292 | A | * | 10/1994 | Hoftman et al. .............. 362/400 |
| 5,465,461 | A | * | 11/1995 | Sandel ............................. 16/421 |
| 5,469,600 | A | * | 11/1995 | Sandel ............................. 16/421 |
| 5,669,102 | A | * | 9/1997 | Sandel ............................. 16/421 |
| 5,697,123 | A | * | 12/1997 | Gharibian et al. .............. 16/422 |
| 5,700,085 | A | * | 12/1997 | Calderwood ................. 362/399 |
| 5,709,465 | A | * | 1/1998 | Lanzone ....................... 362/400 |
| 5,735,598 | A | * | 4/1998 | Ramirez ....................... 362/400 |
| 5,772,316 | A | * | 6/1998 | Hoftman et al. .............. 362/400 |
| 5,803,905 | A | * | 9/1998 | Allred et al. .................. 600/249 |

(Continued)

OTHER PUBLICATIONS

Ecolab USA Inc., PCT/US2013/058029 filed Sep. 4, 2013, "Notification of Transmittal of the International Search Report and the Written Opinion of the international Searching Authority, or the Declaration", mailed Nov. 12, 2013.

*Primary Examiner* — Victor Batson
*Assistant Examiner* — Jason W San
(74) *Attorney, Agent, or Firm* — McKee, Voorhees & Sease

(57) ABSTRACT

The invention is a disposable cover handle cover for a surgical light head, and more particularly to a single-piece, integrally-formed disposable handle cover for a surgical light head and the like. The disposable cover includes a single-piece hollow member having a first open end adapted to receive the positioning handle of the surgical light head housing a camera and a second open end generally opposite the first end. The second end is closed off by a lens disposed within and integral with the hollow body.

10 Claims, 4 Drawing Sheets

(56) References Cited

U.S. PATENT DOCUMENTS

| | | | |
|---|---|---|---|
| 5,884,996 A * | 3/1999 | Cottone et al. | 362/399 |
| 6,370,735 B1 * | 4/2002 | Horan et al. | 16/422 |
| 6,390,659 B1 * | 5/2002 | Saad et al. | 362/572 |
| 6,442,802 B1 * | 9/2002 | Horan et al. | 16/422 |
| 6,447,149 B1 * | 9/2002 | Kaforey et al. | 362/400 |
| 6,546,594 B1 * | 4/2003 | Wills | 16/412 |
| 6,558,068 B1 * | 5/2003 | Wittig | 404/9 |
| 6,644,837 B2 * | 11/2003 | Borders et al. | 362/399 |
| 6,692,141 B2 * | 2/2004 | Jesurun et al. | 362/399 |
| 6,715,904 B2 * | 4/2004 | Naughton | 362/399 |
| 6,847,490 B1 * | 1/2005 | Nordstrom et al. | 359/642 |
| 6,854,866 B1 * | 2/2005 | Liang | 362/399 |
| 6,863,422 B2 * | 3/2005 | Jesurun et al. | 362/399 |
| 7,311,410 B2 * | 12/2007 | Marka | 362/33 |
| 7,695,432 B2 * | 4/2010 | Scheyer | 600/184 |
| 7,757,352 B2 * | 7/2010 | Halamish et al. | 16/421 |
| 8,014,666 B2 * | 9/2011 | Neiman | 396/533 |
| 2002/0089857 A1 | 7/2002 | Borders et al. | |
| 2003/0014834 A1 * | 1/2003 | Naughton | 16/110.1 |
| 2003/0161158 A1 * | 8/2003 | Jesurun et al. | 362/399 |
| 2003/0210559 A1 * | 11/2003 | Jesurun et al. | 362/572 |
| 2006/0088315 A1 * | 4/2006 | Kappali et al. | 396/535 |
| 2008/0131113 A1 * | 6/2008 | Chang | 396/529 |
| 2011/0135295 A1 * | 6/2011 | Gharibian | 396/448 |
| 2012/0075832 A1 * | 3/2012 | Schmid et al. | 362/33 |
| 2013/0127309 A1 * | 5/2013 | Wyner et al. | 312/223.1 |

* cited by examiner

DISPOSABLE HANDLE COVER FOR A SURGICAL LIGHTHEAD

BACKGROUND OF THE INVENTION

1. Field of the Invention

This invention relates generally to a disposable handle cover for a surgical light head, and more particularly to a single-piece, integrally-formed disposable handle cover for a surgical light head and the like.

2. Description of Prior Art

Light heads used in sterile environments, such as in an operating room and/or surgical surroundings, are often handled during a procedure to adjust the angle and position of the light and/or camera in the handle of the light head. Disposable covers for protecting the sterility of these fixtures often are constructed of several assembled pieces resulting in unnecessary manufacturing, handling and shipping expenses.

The present invention addresses these problems and provides a unitarily formed single-piece cover for the handle of a surgical light head that is disposable.

In addition, the present invention addresses these problems by providing a unitarily formed single-piece cover for the handle of a surgical light head that can be formed in a single process of one part.

SUMMARY OF THE INVENTION

In one embodiment, the invention is a disposable cover for a camera housed in a positioning handle of a surgical light head. The cover includes a single-piece, hollow member having a first open end adapted to receive the positioning handle of the surgical light head housing the camera and a second open end generally opposite the first end. The second end is closed off by a lens disposed within and integral with the hollow body. In a preferred form, the lens is recessed from the second end within the hollow body to protect the lens from unwanted contact.

In another embodiment, the invention is an injection molded disposable cover for a camera housed in a positioning handle of a surgical light head. The cover includes an injection molded, single-piece hollow member having a first open end adapted to receive the positioning handle of the surgical light head housing the camera and a second open end generally opposite the first end. A molded lens integral with the hollow body is disposed at and recessed within the second end. In a preferred form, the outside surface of the hollow member is textured and generally translucent, and the lens is transparent to allow light to pass through to the camera within the handle of the surgical light head.

In another embodiment, the invention is a method for forming a disposable camera cover for a camera housed in a positioning handle of a surgical light head. The method includes injecting resin into a mold having a form of a hollow member. The hollow member includes a first open end adapted to receive the positioning handle of the surgical light head housing the camera and a second open end generally opposite the first end. A lens integral with the hollow body is disposed at and recessed within the second end. In a preferred form, the method includes forming the lens and hollow member together as a single-piece within the mold.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings, in which:

DETAILED DESCRIPTION OF THE PREFERRED EMBODIMENTS

Figure 1:
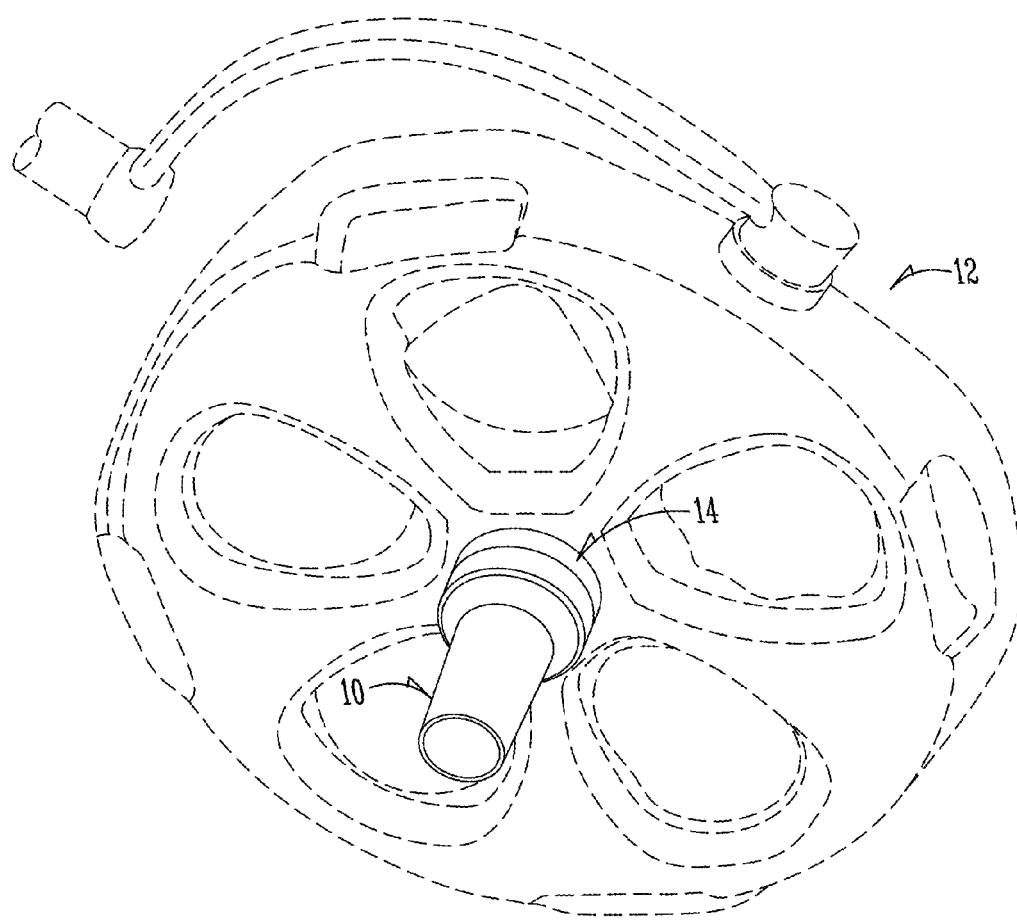
FIG. 1 is a perspective view of surgical light head with a handle covered by a disposable cover according to one aspect of the present invention.

Referring to the Figures, there is generally disclosed in FIGS. 1-4 a disposable cover for the handle of a light head (e.g., surgical light head). Surgical light heads, such as the one illustrated by way of example in FIG. 1, are commonly used in sterile environments (e.g., operating rooms) for directing light onto a desired area and capturing video at the same time. Surgical light heads can vary in size, shape and light output. Generally, a surgical light head 12 such as illustrated in FIG. 1 includes a positioning handle 14 that extends generally perpendicularly outward from the light emitting surface. Video capturing (e.g., camera) equipment is generally housed within the handle 14. The camera in the handle 14 is configured to capture images/video from surgical procedures and/or for clinical teleconferencing. Using the handle 14 a physician or technician is able to control the position and direction of the camera in the handle 14 and the light emitted from the light head.

Figure 2:
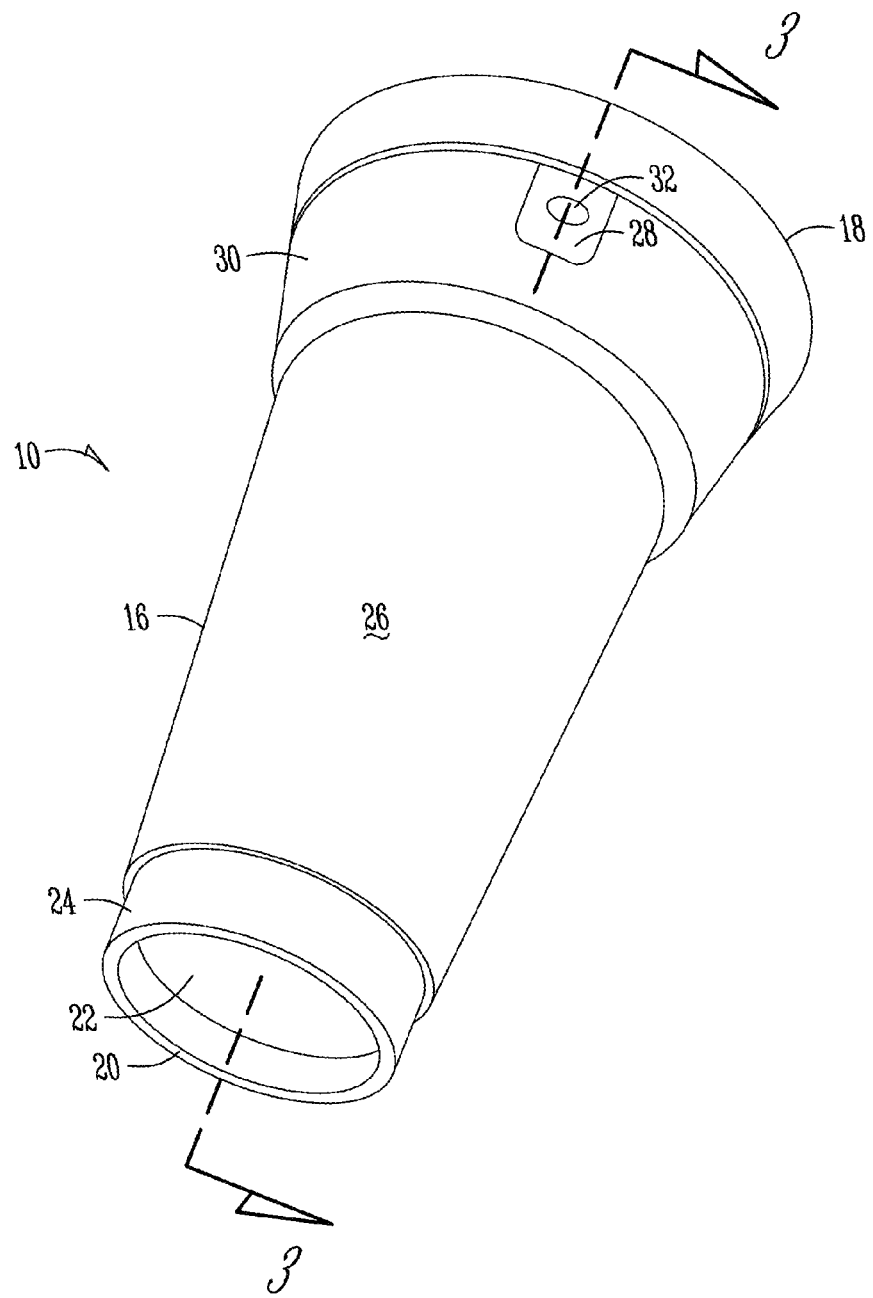
FIG. 2 is a perspective view of the disposable cover shown in FIG. 1.
Figure 3:
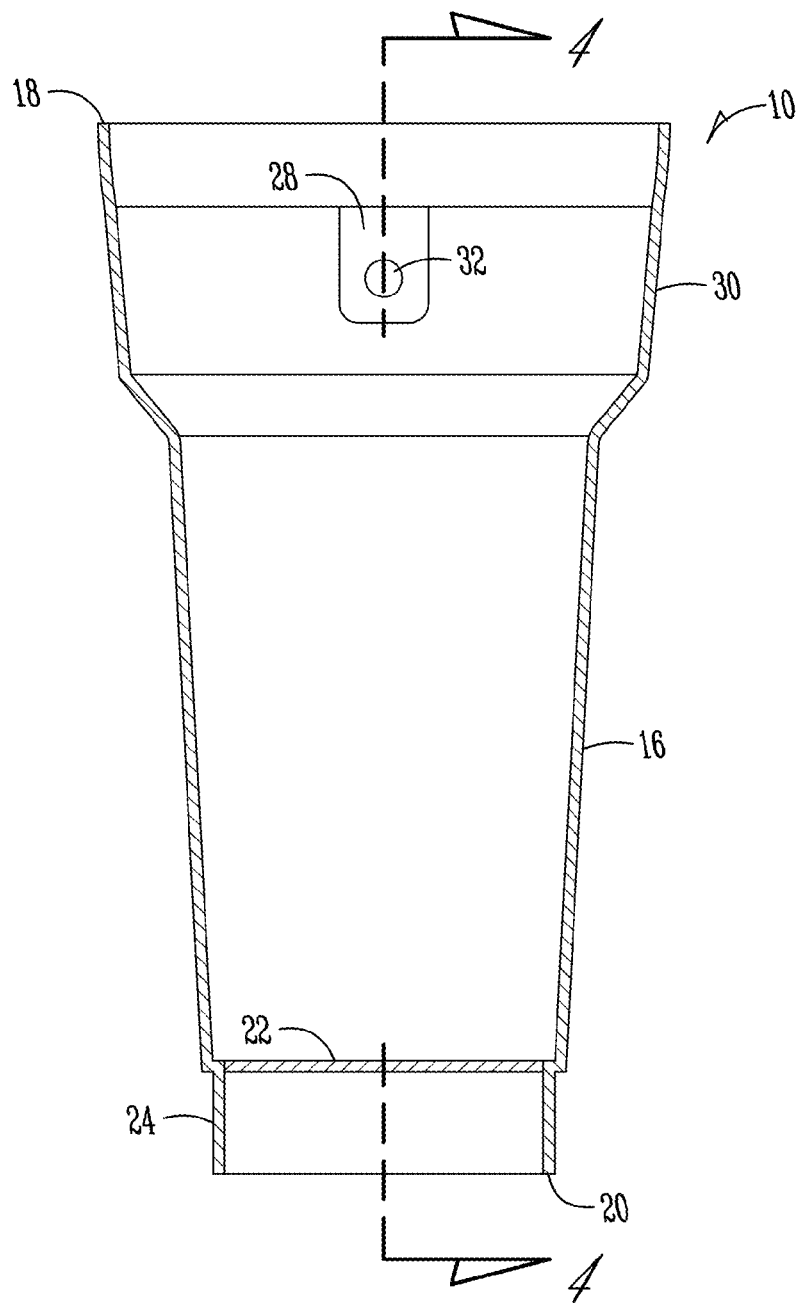
FIG. 3 is a sectional view of the disposable cover taken along line 3-3 in FIG. 2.

As best illustrated in FIGS. 2-3, the cover 10 comprises a generally elongated hollow body or member 16. The body 16 is generally cylindrical or tubular in shape. The body 16 includes a first end 18 that is open. When the cover 10 is mounted on the handle 14, the handle 14 is received into the body 16 through the open first end 18 of the cover 10. The body also includes a second end 20 opposite the first end 18 of the cover 10. In one aspect of the invention, the contour of the body 16 tapers generally from a larger to smaller profile from the first end 18 to the second end 20. In another aspect of the invention, the first end 18 of the body 16 includes a collar 30 having a generally larger diameter profile to accommodate a collar on the handle 14 of the light head 12. The body 16 of the cover 10 from the collar 30 to the second end 20 is generally tubular (i.e., a fixed diameter along this defined length). The second end 20 terminates in a rim 24. A lens 22 is recessed within the body 16 of the cover 10 behind the rim 24. The lens 22 extends across the body 16 of the cover 10 to close off the second end 20 at an optimal depth (e.g., ½-¾ of an inch) behind the rim 24. The lens 22 is recessed within the second end 20 behind the rim 24 to protect the lens from incidental or unwanted contact. The thickness of the sidewalls of the body 16 and lens 22 are generally thin (e.g., 80-120 thousandths of an inch).

Figure 4:
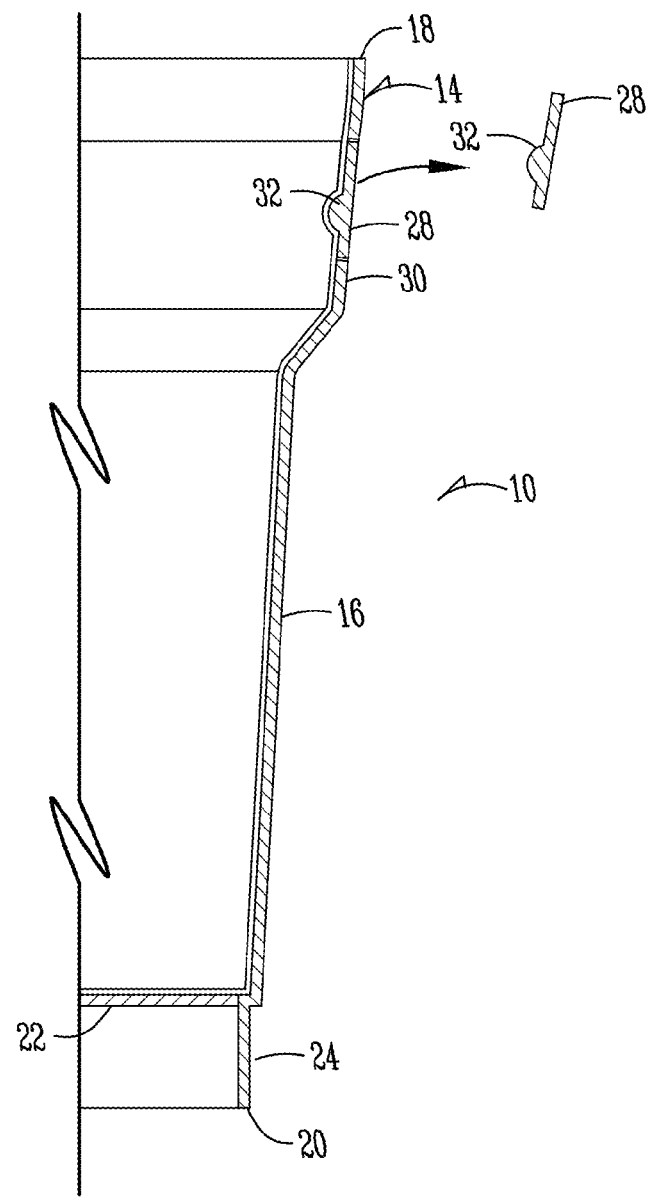
FIG. 4 is a perspective view of the removable tab shown according to one aspect of the present invention.

In one aspect of the invention, the collar 30 is configured to secure the cover 10 to the handle 14 of the light head 12. For example, the collar 30 includes a tab 28 (as best illustrated in FIG. 4) having a detent 32 that creates an interference fit against the outside surface of the handle 14 or a counter reciprocal feature on the outside surface of the handle 14. The interference between these features removably secures the cover 10 to the handle 14 to prevent the cover 10 from unintentionally separating from the handle 14, particularly during manipulation of the light head 12. According to one aspect of the invention, the tab 28 is perforated along edges contiguous with the collar 30 to allow the tab 28 and detent 32 to be separated from the collar 30 to prevent reuse of the cover 10.

The cover 10 is preferably manufactured or produced as a single-piece. In one aspect, the lens 22 is single unitary piece integral with the body 16 of the cover 10. The cover 10 is preferably injection molded as a single, unitary piece. In a preferred form, the cover 10 is injection molded from a clear thermoplastic resin, such as for example, a polycarbonate material. Other thermoplastic materials, that are preferably clear, are also contemplated such as urethane, polystyrene, polyethylene, polymethyl methacrylate, etc. The mold is configured with cosmetic texturing (e.g., by in-mold texturing) to create a frosted appearance of the surface 26, such as a textured, generally translucent appearance. The lens 22 is left untextured (e.g., polished steel tooling is used for surfaces of the mold forming the lens 22) and possesses the optically-clear, transparent properties of the clear thermoplastic material used to form the cover 10. In this embodiment, the lens 22 is configured of the same material used to produce the body 16 of the cover 10 and is molded-in with the body 16 of the cover 10, for example, during the injection molding process.

The single-piece construction of the cover 10 prevents the unnecessary and unwanted handling, shipping and stocking of multiple parts for constructing a single handle cover. The rim 24 extending outward from the lens 22 also helps to protect the lens 22 from being damaged, scratched, scuffed or dirtied during handling, packaging, shipping, attachment and/or use. The cosmetically frosted surface 26 of the body 16 camouflages smudges and other contrasting marks received during handling, packing, shipping, attachment and/or use. Text and other advertising/branding artwork and text can also be included on the surface 26 and be clearly visible due to the contrasting frosted surface 26 of the cover 10.

The above specification, examples, and information provide a description of the manufacture and use of the compositions of the invention. Since many embodiments of the invention can be made without departing from the spirit and scope of the invention, the invention resides in the claims hereinafter appended.

What is claimed is:

1. A disposable cover for a camera housed in a positioning handle of a surgical light head, comprising:
    single-piece hollow member having:
    a. a first open end adapted to receive the positioning handle of the surgical lighthead housing the camera;
    b. a collar extending from the first open end, the collar having a diameter and a length;
    c. a lens disposed within the hollow members;
    d. a sidewall extending between the collar and the lens, the sidewall having a diameter which is smaller than the diameter of the collar and a length which is longer than the length of the collar, the sidewall having a textured outer surface;
    e. a rim extending between the lens and the second end, the rim having an inner diameter which is smaller than the diameter of the sidewall; and
    f. wherein the collar, sidewall, lens, and rim are a single continuous piece of translucent material.

2. The cover of claim 1 wherein the tubular body is tapered generally between the first and second ends.

3. The cover of claim 1 wherein the lens is transparent to allow light to pass through to the camera within the handle of the surgical light head.

4. The cover of claim 1 further comprising a tab integral to the hollow member at the first end, the tab removed to prevent reuse of the cover.

5. An injection molded disposable cover for a camera housed in a positioning handle of a surgical lighthead, comprising:
    an injection molded, single-piece hollow member having:
    a. a first open end adapted to receive the positioning handle of the surgical light head housing the camera;
    b. a collar extending from the first open end, the collar having a diameter;
    c. a second end generally opposite the first end;
    d. a lens integral with the hollow member disposed at and recessed from the second end;
    e. a sidewall which is between 80 and 120 thousandths of an inch thick, the sidewall extending between the collar and the lens, the sidewall having a diameter which is smaller than the diameter of the collar, the sidewall having a textured outer surface; and
    f. wherein the lens and the hollow member are a single continuous piece of translucent material.

6. The cover of claim 5 wherein the second end comprises a rim protruding outward from the lens.

7. The cover of claim 5 wherein the tubular body is tapered generally between the first and second ends.

8. The cover of claim 5 wherein the lens is transparent to allow light to pass through to the camera within the handle of the surgical light head.

9. The cover of claim 5 further comprising a tab integral to the hollow member at the first end, the tab removed to prevent reuse of the cover.

10. The disposable cover of claim 1 wherein the lens is recessed between ½ and ¾ of an inch from the second end.

* * * * *